United States Patent [19]

Harris

[11] Patent Number: 4,585,013
[45] Date of Patent: * Apr. 29, 1986

[54] LUMENLESS PERVENOUS ELECTRICAL LEAD AND METHOD OF IMPLANTATION

[75] Inventor: Donald L. Harris, Miami Beach, Fla.

[73] Assignee: Cordis Corporation, Miami, Fla.

[ * ] Notice: The portion of the term of this patent subsequent to Aug. 28, 2001 has been disclaimed.

[21] Appl. No.: 495,636

[22] Filed: May 18, 1983

Related U.S. Application Data

[63] Continuation-in-part of Ser. No. 255,703, Apr. 20, 1981, abandoned.

[51] Int. Cl.⁴ ............................................. A61N 1/05
[52] U.S. Cl. .................................... 128/785; 128/786; 128/419 P
[58] Field of Search ............................... 128/784–786, 128/419 P, 640, 642

[56] References Cited

U.S. PATENT DOCUMENTS

| | | | |
|---|---|---|---|
| 3,087,486 | 4/1963 | Kilpatrick | 128/419 P |
| 4,102,331 | 7/1978 | Grayzel et al. | 128/640 |
| 4,198,991 | 4/1980 | Harris | 128/784 |
| 4,236,529 | 12/1980 | Little | 128/785 |
| 4,243,050 | 1/1981 | Littleford | 128/784 |
| 4,248,237 | 2/1981 | Kenny | 128/419 P |
| 4,301,815 | 11/1981 | Doring | 128/419 P |
| 4,327,747 | 5/1982 | Gold | 128/419 P |
| 4,467,817 | 8/1984 | Harris | 128/786 |

FOREIGN PATENT DOCUMENTS

| | | | |
|---|---|---|---|
| 2446001 | 9/1980 | France | 128/786 |
| 7909050 | 6/1980 | Netherlands | 128/786 |
| 1219017 | 1/1971 | United Kingdom | 128/419 P |

Primary Examiner—Lee S. Cohen
Attorney, Agent, or Firm—Henry W. Collins; Thomas R. Vigil

[57] ABSTRACT

A lead for connecting an electrical stimulation generator to an internal organ of the body via the vascular system includes a small diameter nonhollow multifilament lead body surrounded by a guide sleeve. The guide sleeve pushes against a sleeve stop at the distal end of the lead to impart axial motion to the lead with stylet-like action. After the lead electrode is properly positioned, the sleeve is removed by severing it longitudinally as it is pulled off of the lead. A plurality of radially deployable folding fins are arranged on the distal portion of the lead so that they can be wrapped around the lead body without overlap even though the combined length of the fins in one embodiment is greater than the circumference of the lead body. The electrically conductive core of the lead is preferably comprised of thousands of carbon filaments embedded in a resin matrix.

11 Claims, 7 Drawing Figures

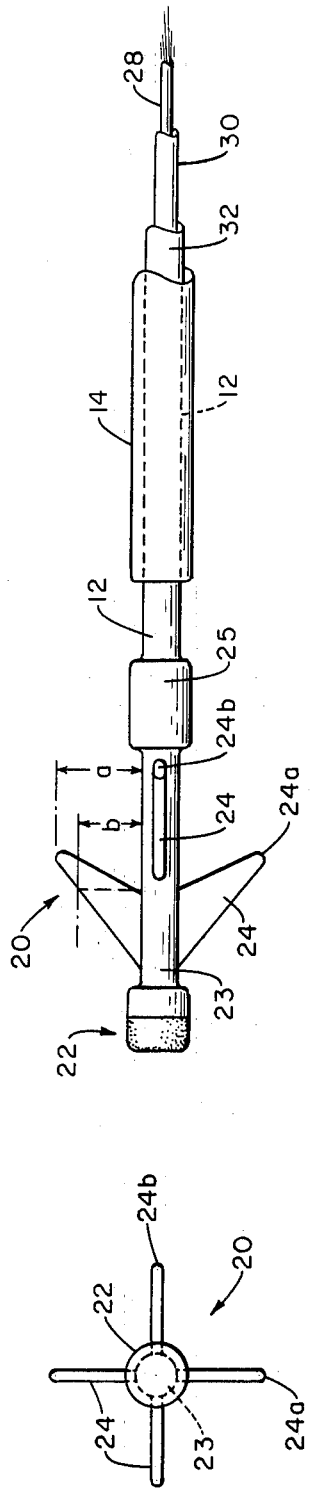
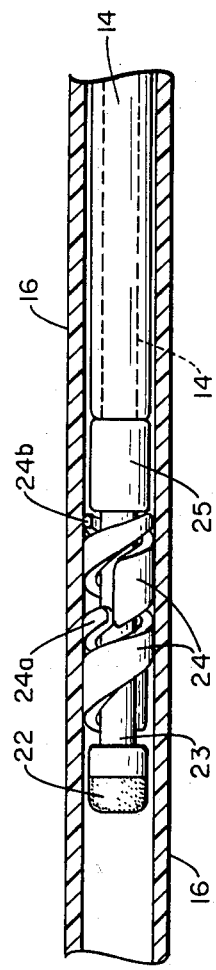
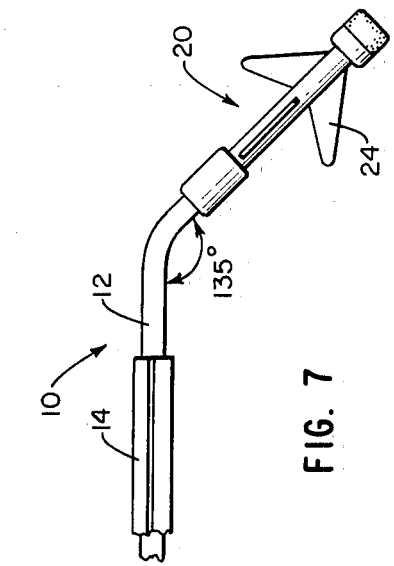
FIG. 3
FIG. 4
FIG. 5
FIG. 6
FIG. 7

LUMENLESS PERVENOUS ELECTRICAL LEAD AND METHOD OF IMPLANTATION

REFERENCE TO RELATED APPLICATION

The application is a continuation-in-part of U.S. patent application Ser. No. 255,703 by Donald L. Harris which was filed on Apr. 20, 1981 and is assigned to the assignee of the present application now abandoned in favor of continuation application Ser. No. 495,451, filed May 18, 1983, now U.S. Pat. No. 4,467,817.

BACKGROUND OF THE INVENTION

This invention relates to electrical leads, and more particularly to a lead which connects a source of electrical signals to an organ of the body such as the heart.

It is known to stimulate internal body organs such as the heart with electrical signals generated by an electronic device such as a pacemaker. These signals compensate for various cardiac dysfunctions such as rhythm disorders. Generally, the pacing device itself is located some distance away from the organ needing stimulation and is connected to the organ by an electrical lead.

One way of establishing electrode contact with heart muscle is to feed the electrode and its lead through the venous system into the heart. It is necessary in this case that the lead somehow be imparted with sufficient stiffness and maneuverability to negotiate the various turns encountered in the journey through the venous system to the heart. Once installed, the lead must have sufficient flexibility to withstand the continuous motion of the body over many years without undue mechanical stress. It is also desirable that a stimulating lead have small diameter to lessen interference with blood flow, to facilitate introduction into the vascular system and to accommodate multiple lead systems.

In the prior art, it is known to employ a lead with a central hole or lumen inside a long hollow coil of electrically conductive wire. A relatively stiff guide wire or stylet is inserted into the lumen as an aid for feeding the lead through the venous system. The stylet is fed through the lead all the way until it encounters the closed distal end of the lead. As the physician continues to push the proximal end of the stylet, the stylet transmits axial force to the electrode end of the lead. The lead in turn is driven, or actually pulled forward from the distal end. Observing the position of the end of the lead on a fluoroscope during the procedure, the physician quickly "threads" the lead through the vascular system by manipulating the stylet from the outside. Physicians specializing in implantation of cardiac pacers, for example, are used to the foregoing procedure and have highly developed skills which enhance confidence in the procedure. The ease and familarity of the stylet procedure also help reduce the trauma to the patient while insuring positive placement of the lead. Once the lead is installed, the stylet is removed. The remaining overall lead diameter, of course, is larger than would have been the case without the stylet-receiving lumen.

The electrodes on the distal ends of prior art cardiac stimulating leads are frequently equipped with protruding tines or fins to aid in attachment to the inside wall of the heart. These prior art electrodes were of relatively large diameter requiring a large diameter introducer sheath for entry into the vascular system. In addition, the need to restrict the overall diameter of the electrode required that the fins be kept small. Small fins, however, provide insufficient "anchoring".

It is, therefore, an object of the present invention to provide an extremely flexible stimulating lead with a reduced diameter while preserving stylet-like action during the implantation procedure.

It is a further object of the present invention to provide a lead having a distal tip of smaller diameter and longer fins without unduly increasing the overall diameter of the lead during introduction into the vascular system.

SUMMARY OF THE INVENTION

According to the present invention a small diameter lumenless flexible pervenous lead is formed by a plurality of conductive carbon filaments, preferably embedded in a resin matrix, within an insulating cover. An electrode is secured to the distal end of the lead and a connector is mounted at the proximal end of the lead adapted for connection to an electrical stimulation generator. During manufacture, a slidable guide sleeve is placed over substantially the entire length of the lead body. The distal end or tip of the lead itself has a larger diameter than the lead body so that the distal end of the guide sleeve can abut the back of the tip and drive the lead forward with stylet-like action. Thus the guide sleeve serves as an external stylet. After installation the sleeve is removed by severing it longitudinally as it is pulled off the lead body. In the preferred embodiment, the guide sleeve has a pair of longitudinally extending separating grooves to allow the sleeve to be peeled from the lead.

In another aspect of the invention, the electrode includes a body portion with an electrode tip and a plurality of resilient hooking fins extending radially from the body portion. The blade-like fins attach to the cylindrical tip parallel to its axis and fold circumferentially without overlapping when the lead is twisted during insertion through a closely fitting conventional introducer sheath which form the entry into the blood vessel. Two embodiments are shown. In one, the fins are mounted at staggered axial locations. This arrangement permits the combined length of the fins to exceed the circumference. In the other embodiment, three equally spaced fins are mounted at the same axial location along the tip. Each fin has a length just less than one-third of the circumference to avoid overlapping. After introduction, the fins self-deploy due to their intrinsic resilience.

BRIEF DESCRIPTION OF THE DRAWING

The invention disclosed herein may be better understood with reference to the following drawing of which:

FIG. 3 is a side view of the distal portion of the lead and guide sleeve of FIG. 1;

FIG. 4 is a front distal end view of the lead of FIG. 3;

FIG. 5 is a diagrammatic representation of the distal portion of the lead of FIGS. 1 and 3 being inserted through the introducer sheath with the fins wrapped around;

FIG. 6 is a diagrammatic representation of a front distal end view of another embodiment of the fins; and FIG. 7 is a diagrammatic representation of the lead of FIG. 1 with a preformed bend.

DESCRIPTION OF THE PREFERRED EMBODIMENT

Figures 1, 2:
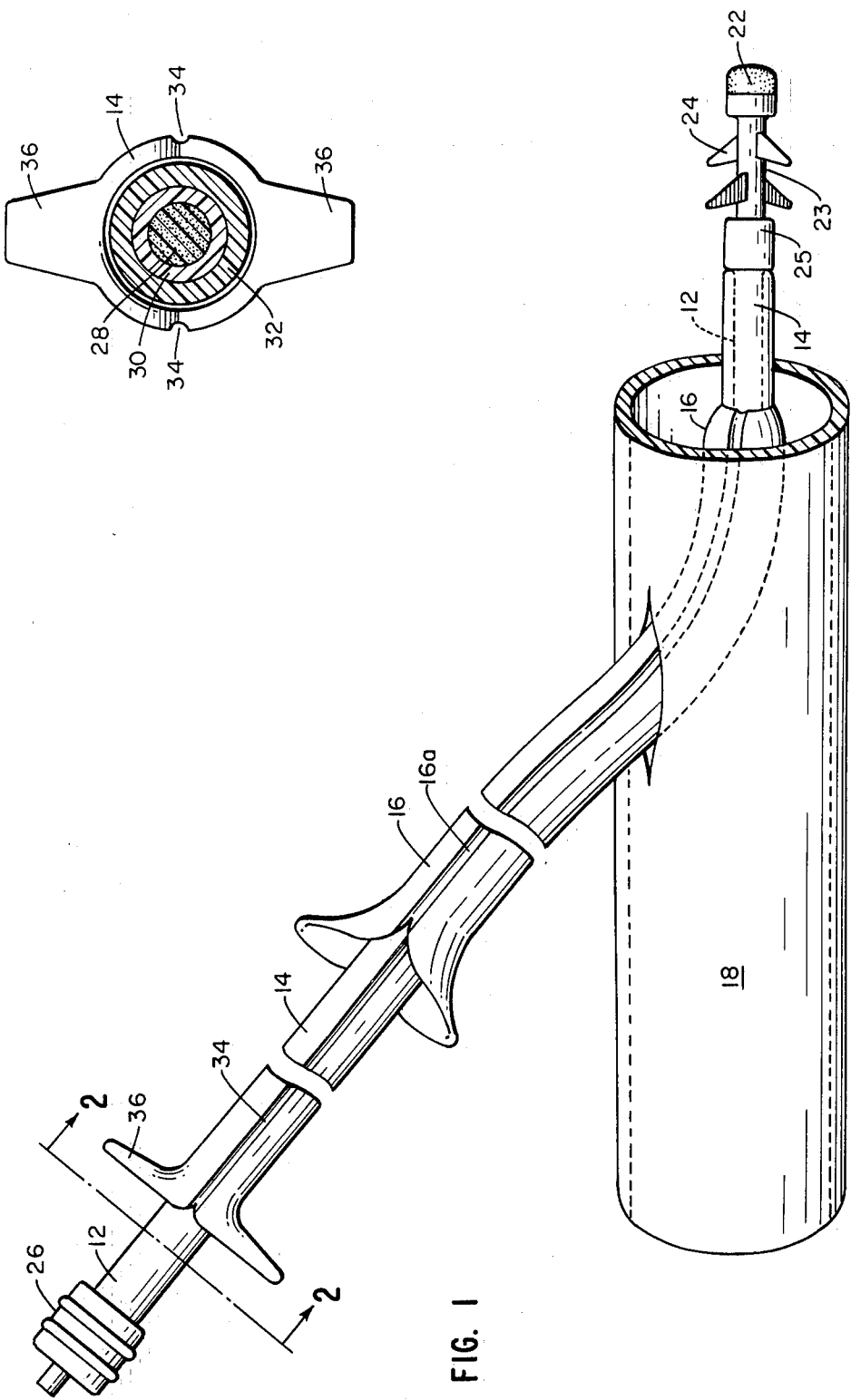
FIG. 1 is a diagrammatic representation of the lead disclosed herein being introduced into the vascular system via an introducer sheath.
FIG. 2 is a cross-sectional view of the lead system of FIG. 1 taken at lines 2—2.

In the embodiment of FIG. 1, a small diameter lumenless pervenous unipolar cardiac pacer lead system is designated generally at 10. The lead system 10 includes an insulated multifilament, small diameter, elongated, flexible lead body 12 surrounded by a guide sleeve 14. As illustrated, the lead system 10 is inserted through a conventional split sheath introducer 16 into a blood vessel 18 of the vascular system. The distal end of the lead body 12 terminates in an electrode assembly 20 (FIG. 3) which includes a distal electrode tip portion 22, an intermediate cylindrical body portion 23 of reduced diameter with four blade-like radial hooking fins 24, and a proximal annular enlargement forming a sleeve stop 25. The sleeve stop 25 and electrode tip 22 preferably have the same diameter as the outer diameter of the guide sleeve 14. The hooking fins are used to aid in attaching the electrode assembly 20 by snaring the trabeculae of the heart. Fibrotic growth also tends to envelop and ensnare the fins after implantation. The proximal end of the lead body 12 terminates in a connector 26 for a conventional cardiac power.

The multifilament lead body 12 has a diameter of approximately 0.053 inches which corresponds to a French 4 diameter. As shown in FIGS. 2 and 3, the lead body 12 is composed of a core 28 comprising a bundle of thousands of tiny carbon fibers (preferably 3000) in a high modulus graphite filament form. Suitable fiber material is available from the Union Carbide Corporation under the trademark "Thornel" and is designated as 300 WYP 30 1/0 with a special resin matrix added. Under this designation, the fibers are embedded in a resin matrix composed of tetrafluoroethylene mixed with a small proportion of urethane as described in U.S. Pat. No. 4,198,991, entitled "Cardiac Pacer Lead", the teachings of which are incorporated herein by reference. The core 28 is then pulled into a thin-walled tube 30 of polytetrafluoroethylene manufactured by Dupont and designated 6C having good lubricity and long flex life both to contain the fibers and to act as an electrical insulator. The combination of the tubing and resin matrix prevents the fibers from breaking or otherwise destroying one another as the lead 12 flexes both during introduction into the vascular system and thereafter during its intended operation. The core 28 and tube 30 assembly is next pulled into a body compatible polyurethane tube 32. A suitable tube 32 material is available from Mobay Chemical Corporation of Pittsburgh, Pa. under the designation Texin 85-A. The polyurethane tube 32 is first allowed to expand in chlorothene for fifteen to thirty minutes before being pulled over the core 28-tube 30 assembly. The polyurethane tube 32 is then allowed to shrink by exposure to air. The lead body 12 is thus of solid construction since a lumen is not needed as in the prior art systems which use an internal stylet to guide the lead to the heart.

The multifilament lead body 12 is surrounded by the guide sleeve 14 which is adapted to impart axial force to the distal end to drive the lead 12 through the vascular system. The sleeve 14 is a substantially cylindrical jacket preferably made of a high density polyethylene such as Marlex HHM 4903 available from Phillips Petroleum, and compounded with approximately 10% barium sulphate and 1% titanium dioxide to make the sheath radiopaque and white. The sleeve 14 slides over the lead body 12 at the time that the lead system 10 is manufactured. Thus it comes "built-on" the lead. The sleeve 14 has a wall thickness of approximately 0.0065 inch, so that the combined lead body 12 and sleeve 14 diameter is approximately 0.066 inches corresponding to a French 5 diameter. Because the inner diameter of the sleeve 14 is less than or equal to the cross-sectional diameter of the sleeve stop 25 of the electrode assembly 20 diameter (approximately 0.079 inch), the sleeve 14 acts as a pusher for guiding the electrode assembly 20 to the target organ. After the sleeve 14 is assembled onto the lead body 12, the electrode assembly 20 and connector 26 are affixed to the distal and proximal ends of the lead respectively in an electrically conducting relation in the manner described in the above-mentioned U.S. Pat. No. 4,198,991.

The guide sleeve 14 serves only to drive the lead through the vascular system to the target organ; it must be removed once the electrode assembly 20 is properly positioned. It cannot be removed by sliding it off because its diameter is much smaller than that of the connector 26 over which it would have to be removed. (It could be removed by sliding it from the lead body 12 if the connector 26 were not attached to the lead until the lead had been positioned within the body. However, the connector 26 then would have to be attached to the lead in the midst of a sterile procedure, a practical impossibility.) A similar problem is encountered in removing the short introducer sheath 16 (FIG. 1). As explained in U.S. Pat. No. 4,166,469 to Littleford, the introducer sheath is equipped with means defining longitudinal weakening lines 16a so that the introducer can be split and peeled apart to remove it from the lead. According to the present invention, the guide sleeve 14 is also rendered readily removable by providing it with longitudinally extending separating grooves 34 over its entire length, i.e. substantially the length of the lead. The sleeve 14 can be peeled apart by grasping the handles 36 and pulling gently. The handles 36 are molded onto the sheath 14. The grooves 34 are approximately 0.005 inch deep which represents an 80% to 90% cut through the wall of the sheath 14. Such a groove assures that the sleeve 14 will separate readily. As shown in FIG. 1, during introduction into the vessel, the lead 12 is surrounded by two split "sheaths", the long guide sleeve 14 and the short introducer 16.

The electrode assembly 20 comprises the electrode tip portion 22 which is adapted for engaging the organ to be stimulated in an electrically conducting relationship. The electrode 22 is of conventional design with a diameter of approximately 0.079 inch and may be porous or nonporous. A suitable material is elgiloy or platinum, or even an extension of the carbon fibers themselves. At the other end of the electrode body 23, the sleeve stop 25 halts the forward motion of the sleeve 14 in relation to the lead 12. By preventing further forward motion of the sleeve 14 independent of the lead, the sleeve stop 25 forces the sleeve 14 to push the electrode assembly 20 through the venous system to the heart.

The electrode assembly 20 is specifically adapted to anchor the tip of the lead inside the heart. The hooking fins 24 become ensnared in the fine tangled trabeculae of the heart wall to immobilize the electrode assembly 20 with respect to the heart muscle. The four blade-like fins 24 (FIGS. 3 and 4) are made of a thin, flexible material such as silastic or polyurethane. When the lead is twisted, the fins 24 fold circumferentially without overlap and the diameter is small enough so that it may be inserted through an introducing assembly used for a French 7 diameter lead (FIG. 5). Once the electrode assembly 20 has passed through the introducing assembly 16, the resilient fins 24 resume their deployed state.

As shown in FIGS. 3 and 4, the preferred staggered fin arrangement comprises a first pair of opposed coplanar fins at 0° and 180° with respect to the orientation of the first fin about the lead body axis and a second pair of opposed coplanar fins at 90° and 270° axially spaced from the first pair. By design the fins' deployed radial length is about three-fourths of a circumference, expressed as $a=3/2(\pi r)$, where r is the radius of the lead body 23. To avoid overlapping the opposed fin of the same pair, the distance b, i.e., the radial extent of the fin from the rear attachment point of the fin to the lead body must be less than a half circumference or $b<\pi r$. This relationship governs the angle of the fin. The first fin in the second pair is attached to the lead body 23 just beyond the point reached by the tip 24a (FIG. 5) of the corresponding fin of the first pair when it is wrapped flat around the lead body. Other geometries are possible. For example, one long fin could be used at each of three axially spaced locations. To avoid overlapping itself, the pitch of the larger fin would be confined to $b<2\pi r$. Each fin, when extended, is flat and parallel to the lead axis. Thus each fin is attached to the cylindrical lead body 23 at a line substantially parallel to the axis.

In the alternate simpler embodiment of FIG. 6, three fins are equally circumferentially spaced at the same axial location and each has a length just under one-third of the circumference of the lead body to avoid overlap. In very small diameter leads, however, this length may offer inadequate anchoring.

In operation, the small diameter lead system 10 is introduced through the sheath 16 into a vessel 18 in FIG. 1. Once the lead has been introduced as shown in FIG. 1, the sheath 16 can be removed by peeling it apart along lines 16a as it is pulled out of the blood vessel. The lead with its electrode assembly 20 is guided through the vascular system by means of the stylet-like action of the external guide sleeve 14.

When the ventricle of the heart is the target organ, the lead must pass through the tricuspid valve of the heart. Because of the location of the tricuspid valve, it is helpful for the distal end of the lead to have a pronounced bend in it so that it can more easily pass through the valve. In prior art devices the removable internal stylet itself was bent to enable passage through the tricuspid valve. In the present embodiment, however, since there is no internal stylet, a portion of the carbon lead body 12 itself about 5 cm. from the distal end of the tip 22 has a pre-formed 135° bend, as shown in FIG. 7. This pre-formed bend is created by heating the lead body 12 in a form so that the tubing over the fibers will take a set upon cooling. While the sleeve 14 covers this pre-formed portion, however, the lead body 12 is straightened. At the tricuspid valve, the sleeve 14 is retracted from the electrode assembly 22 by means of the handles 36 so that the bend in the carbon lead 12 is deployed to navigate the passage through the tricuspid valve. Once the distal portion of the lead has assumed the proper position, the sleeve 14 is advanced to the sleeve stop 25, covering the bend in the lead 12 again to straighten it for its final positioning within the heart.

At the desired location, the hooking fins 24 engage the trabeculae of the heart. After the electrode assembly is securely in place, the sleeve 14, having performed its function of driving the lead to the target organ, is peeled apart as it is withdrawn from the vessel 18 (FIG. 1). The carbon lead body 12 and the electrode assembly 20 remain in the body. With time, fibrotic tissue further ensnares the electrode assembly 20 thus securing the distal end of the lead. If it is desired to remove the lead at some later time, the lead may be twisted to help free the electrode assembly 20 by wrapping the fins around the electrode so that it can be repositioned or withdrawn.

The unipolar embodiment shown in the drawings may be modified to provide a small diameter bipolar lead by interposing a suitable hollow, coaxial conductor (e.g., coiled elgiloy) between the tubes 30 and 32 and placing an electrically connected ring electrode on the sleeve stop 25.

Thus the invention provides a small diameter lumenless lead retaining stylet-like action to aid in its journey through the venous system. The use of the external sleeve eliminates the need for the lead itself to have a hollow interior to accommodate a stylet as known in prior art systems, thereby reducing the overall diameter of the lead. The reduced size is particularly advantageous in multiple lead systems. The carbon filament core provides increased flexibility. In addition, the nonoverlapping folding fin design allows proportionately larger fins without increasing the diameter of the electrode assembly as it passes through the introducer sheath thus minimizing trauma to the patient.

Although this invention has been described with reference to specific embodiments, it is understood that modifications and variations may occur to those skilled in the art. It is intended that all such modifications and variations be included within the scope of the appended claims.

What is claimed is:

1. A pervenous lead system for establishing electrical contact between an electrical stimulation generator and an internal organ, comprising
   an implantable lead with proximal and distal ends having a flexible substantially solid insulated lead body carrying at least one electrical conductor, said proximal end having means for electrically connecting the electrical stimulation generator to the electrical conductor, said lead having a portion of enlarged diameter toward the distal end and an electrode connected thereto in electrical contact with said conductor,
   removable sleeve means slidably mounted on said lead body for applying axial force directly to the enlarged distal portion of said lead including a flexible guide sleeve disposed coaxially and slidably over substantially the entire length of said lead body with a uniform inner diameter between those of said lead body and the enlarged distal portion of said lead such that said sleeve is slidable into abutment with the enlarged distal portion of said lead so as to drive it forward when the sleeve is advanced from the proximal end,
   said enlarged distal portion including guide sleeve stop means proximally spaced along said lead body from said electrode for blocking independent forward movement of the abutting end of the guide sleeve, and a plurality of deployable flexible tissue-engaging projections extending outwardly from said lead body between said sleeve stop means and said electrode.

2. The lead system or claim 1, wherein said guide sleeve stop means includes a sleeve stop, and said projections fold against and conform to the adjacent circumference of the lead body between said sleeve stop and electrode without overlapping when said projections are bent in the same sense around said lead body.

3. The lead system of claim 2, wherein the outer diameter of said guide sleeve, sleeve stop means and electrode are approximately the same, whereby the overall diameter of the lead with the guide sleeve in place and the projections wrapped around the circumference of the lead body is substantially uniform to accommodate a minimum size introducer sheath.

4. A pervenous lead system for establishing electrical contact between an electrical stimulation generator and an internal organ, comprising an implantable lead with proximal and distal ends having a flexible insulated substantially solid lead body containing a plurality of electrically conductive flexible parallel carbon filaments embedded in a resin matrix longitudinally extending from the proximal to the distal end of said lead, said lead having a portion of enlarged diameter toward the distal end and an organ-contacting electrode electrically connected to said carbon filaments, removable flexible sleeve means slidably mounted on said lead body for applying axial force directly to the enlarged distal portion of said lead while traveling through a blood vessel, and means at the proximal end for electrically connecting said carbon filaments to the generator, whereby the lead can be urged flexibly through a blood vessel with stylet-like action by externally manipulating said sleeve means.

5. The lead of claim 4, wherein said organ-contacting electrode has a larger diameter than said lead body.

6. The lead of claim 5, wherein said enlarged diameter portion comprises a raised, ring-like, circumferential projection on said lead body at the distal end axially spaced in the proximal direction from said organ-contacting electrode.

7. The lead of claim 6, further comprising a plurality of tissue-engaging, deployable flexible projections extending from plural locations on the lead body between said organ-contacting electrode and said ring-like projection.

8. The lead of claim 7, wherein the diameters of the ring-like projection and the organ-contacting electrode are substantially the same and said tissue-engaging projections are positioned and sufficiently flexible to fold against and conform to the circumference of the lead body, said projections having a maximum thickness less than the difference between the diameter of the organ-contacting electrode and ring-like projection on the one hand and the intermediate lead body on the other hand.

9. A method of implanting a lumenless electrical lead through the vascular system of the body, comprising the steps of providing a lead system comprising a lead having a flexible, substantially solid, insulated, electrically conductive lead body with a proximal and distal end, said lead including a connector electrically connected to the proximal end of said lead body and an electrode assembly electrically connected to its distal end, said lead system further including a removable guide sleeve covering said lead body, the distal end portion of said lead having an enlargement acting as a guide sleeve stop, introducing said lead system, distal end first, into a blood vessel through a removable introducer sheath, removing the introducer sheath by severing it longitudinally while peeling it off of the lead system after a portion of the lead system has been inserted into the blood vessel, driving the lead through the vascular system by pushing on the proximal end of the sleeve so that the distal end of the sleeve abuts against the sleeve stop and forces the distal end portion of the lead forward, and after attaining the desired location for the distal portion of the lead, removing the guide sleeve from the lead body by severing the guide sleeve longitudinally while pulling it off of the lead body.

10. The method of claim 9, wherein said lead body has a resilient, preformed distal bend proximally spaced from said enlargement and the method further comprises the steps covering and thereby straightening the bend with the guide sleeve while advancing the lead through the vascular system to a predetermined point therein, partially retracting said guide sleeve to uncover and thereby deploy said preformed bend to assist in navigating a particular portion of the vascular system, and resuming the advancing of said lead by sliding the sleeve into engagement with said sleeve stop thereby covering and restraightening the bend.

11. The method of claim 9, wherein the distal portion of said lead carries a plurality of flexible fins and the method further comprises the step of twisting the lead axially while advancing the distal end of the lead through the introducer sheath to wrap the fins around the circumference of the lead without overlapping the fins.

* * * * *